(12) United States Patent
Oishi et al.

(10) Patent No.: US 11,878,101 B2
(45) Date of Patent: Jan. 23, 2024

(54) BLOOD PURIFICATION DEVICE AND METHOD FOR PRODUCING SAME

(71) Applicant: ASAHI KASEI MEDICAL CO., LTD., Tokyo (JP)

(72) Inventors: Teruhiko Oishi, Tokyo (JP); Makoto Ozeki, Tokyo (JP); Keitaro Matsuyama, Tokyo (JP); Naoki Morita, Tokyo (JP); Hiroshi Tajima, Tokyo (JP); Toshinori Koizumi, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 532 days.

(21) Appl. No.: 17/041,683

(22) PCT Filed: Mar. 29, 2019

(86) PCT No.: PCT/JP2019/014334
§ 371 (c)(1),
(2) Date: Sep. 25, 2020

(87) PCT Pub. No.: WO2019/189881
PCT Pub. Date: Oct. 3, 2019

(65) Prior Publication Data
US 2021/0008270 A1  Jan. 14, 2021

(30) Foreign Application Priority Data

Mar. 30, 2018 (JP) ................................. 2018-068734

(51) Int. Cl.
*A61M 1/36* (2006.01)
*A61M 1/16* (2006.01)
*A61M 1/02* (2006.01)

(52) U.S. Cl.
CPC ........ *A61M 1/3679* (2013.01); *A61M 1/0231* (2014.02); *A61M 1/0259* (2013.01); *A61M 1/16* (2013.01); *A61M 2205/759* (2013.01)

(58) Field of Classification Search
CPC .... A61M 1/0231; A61M 1/0259; A61M 1/16; A61M 1/3679; A61M 2205/759;
(Continued)

(56) References Cited

U.S. PATENT DOCUMENTS

| 5,877,005 A | 3/1999 | Castor et al. |
| 2002/0020946 A1* | 2/2002 | Hiraoka ............. B29C 71/0009 |
| | | 429/247 |

(Continued)

FOREIGN PATENT DOCUMENTS

| AT | 505690 A1 | 3/2009 |
| CN | 1988926 A | 6/2007 |

(Continued)

OTHER PUBLICATIONS

Supplemental Partial European Search Report issued in EP Patent Application No. 19774668.8, dated Aug. 17, 2021.

(Continued)

*Primary Examiner* — Dirk R Bass
(74) *Attorney, Agent, or Firm* — GREENBLUM & BERNSTEIN, P.L.C.

(57) ABSTRACT

A blood purification device includes a porous molded body containing an inorganic ion-adsorbing material and is characterized by the following: the concentrations of Mg, Al, Ti, V, Cr, Mn, Fe, Ni, Cu, Zn, Ga, Rb, Sr, Y, Zr, Mo, Ru, Ag, Cd, Sn, Cs, La, Pr, Sm, Gd, Tb, Ta, Au, Tl, Co, In, and Bi are each 0.1 ppb or less and the concentrations of Ba, Nd, Pb, And Ce are each 1 ppb or less in a physiological saline solution for injection both three months and six months after said physiological saline solution for injection is sealed in (Continued)

the blood purification device; and the number of fine particles having a size of 10 μm or more is 25 or less and the number of fine particles having a size of 25 μm or more is 3 or less in 1 mL of the physiological saline solution for injection.

8 Claims, 1 Drawing Sheet

(58) Field of Classification Search
CPC ...... A61M 2207/00; B01J 20/06; B01J 20/08; B01J 20/10; B01J 20/32
See application file for complete search history.

(56) References Cited

U.S. PATENT DOCUMENTS

| | | |
|---|---|---|
| 2002/0060180 A1 | 5/2002 | Sugisaki |
| 2006/0093999 A1 | 5/2006 | Hei |
| 2007/0128424 A1 | 6/2007 | Omori et al. |
| 2008/0314817 A1 | 12/2008 | Fujita et al. |
| 2010/0147768 A1 | 6/2010 | Addleman et al. |
| 2011/0208105 A1 | 8/2011 | Brandl et al. |
| 2013/0190168 A1 | 7/2013 | Wong et al. |
| 2015/0174312 A1 | 6/2015 | Ichi et al. |
| 2016/0250404 A1 | 9/2016 | Simonis |
| 2017/0173231 A1 | 6/2017 | Kiriyama et al. |
| 2018/0326136 A1 | 11/2018 | Morita et al. |
| 2018/0326141 A1 | 11/2018 | Han et al. |
| 2020/0171479 A1 | 6/2020 | Morita et al. |

FOREIGN PATENT DOCUMENTS

| | | |
|---|---|---|
| CN | 103055822 A | 4/2013 |
| CN | 104363933 A | 2/2015 |
| CN | 105916532 A | 8/2016 |
| EP | 1808452 A1 | 7/2007 |
| JP | 61-058664 A | 3/1986 |
| JP | 2002-102335 A | 4/2002 |
| JP | 2004-305915 A | 11/2004 |
| JP | 2006-81759 A | 3/2006 |
| JP | 4671419 B2 | 4/2011 |
| JP | 2016-77570 A | 5/2016 |
| JP | 2017-086563 A | 5/2017 |
| JP | 2017-104852 A | 6/2017 |
| WO | 2011/125758 A1 | 10/2011 |
| WO | 2017/082423 A1 | 5/2017 |
| WO | 2018/212269 A1 | 11/2018 |

OTHER PUBLICATIONS

International Search Report issued in PCT/JP2019/014334, dated Jun. 25, 2019, along with an English translation.
Written Opinion of the ISA issued in PCT/JP2019/014334, dated Jun. 25, 2019, along with an English translation.
International Preliminary Report on Patentability issued in PCT/JP2019/014334, dated Oct. 6, 2019, along with an English translation.
Kocakulak et al., "Effect of poly(2-methoxyethyl acrylate)-coated oxygenators on haemolysis" *J. Biomater. Sci. Polymer Edn*, vol. 17, No. 4, pp. 449-460 (2006).
Makoto Onishi, Surface Modification of Polymeric Materials for Medical Devices, Science of Surfaces, Japan, vol. 32, No. 9, pp. 581-586 (2011), including English language Abstract.
Saito, N. "Cleaning with Supercritical Carbon Dioxide" J. Vac. Soc. Jpn., vol. 43, No. 6, pp. 24-29 (2000), along with a partial English language translation.

\* cited by examiner

BLOOD PURIFICATION DEVICE AND METHOD FOR PRODUCING SAME

FIELD

The present invention relates to a blood purification device comprising a porous molded body that contains an inorganic ion adsorbent, and a method for producing it. More specifically, the invention relates to a blood purification device comprising a porous molded body that contains an inorganic ion adsorbent, which has high phosphorus adsorption capacity and can be safely used, as well as to a method for producing it.

BACKGROUND

Healthy adults with normally functioning kidneys discharge excess phosphorous out of the body primarily through urine. However, kidney disease patients with impaired renal function, such as chronic renal failure patients, are unable to properly excrete excess phosphorus out of the body, and this leads to gradual internal buildup of phosphorus, causing the condition of hyperphosphatemia.

Persistent hyperphosphatemia can lead to secondary hyperparathyroidism, resulting in renal osteopathy with symptoms such as painful and fragile or deformed bones that are prone to fracture, while in cases of concomitant hypercalcemia, the risk of cardiac failure due to calcification of the cardiovascular system also increases.

Cardiovascular calcification is one of the most serious complications of chronic renal failure, and proper control of phosphorus levels in the body is extremely important to prevent hyperphosphatemia in chronic renal failure patients.

For hemodialysis patients, phosphorus that has accumulated in the body is periodically removed and regulated by dialysis treatment by hemodialysis, hemofiltration dialysis or hemofiltration so that hyperphosphatemia does not result. Dialysis treatment usually needs to be carried out three times per week, with a treatment period of 4 hours each time.

However, when a hemodialysis patient ingests the 1000 mg of phosphorus that is ingested per day by a healthy person, the amount of phosphorus that would normally be excreted from the kidneys (650 mg) accumulates in the body, reaching an accumulated amount of 4550 mg within a week. Normal hemodialysis can remove about 800 to 1000 mg of phosphorus with a single dialysis procedure, allowing removal of about 3000 mg of phosphorus by dialysis 3 times a week. Since the amount of phosphorus that can be removed by dialysis treatment (3000 mg) does not match the amount of phosphorus that accumulates each week (4550 mg), accumulation of phosphorus in the body occurs as a result.

Maintenance dialysis patients who are chronic renal failure patients have lost renal function as the major route of phosphorus excretion, and therefore the function of excreting phosphorus into the urine is essentially lost. Since phosphorus is not present in the dialysate from dialysis treatment it is possible to remove phosphorus from the body by diffusion into the dialysate, but at the current time it is not possible to achieve adequate excretion with the currently employed dialysis times and dialysis conditions.

The phosphorus-removal effect of dialysis treatment alone is therefore inadequate, and consequently alimentary therapies and drug therapies with ingestion of phosphorus adsorbents are also used in addition to dialysis treatment to achieve phosphorus control, although it is important that consumption of phosphorus is restricted after having evaluated the nutritional status of the patient and confirmed that there is no malnutrition.

The CKD-MBD (chronic kidney disease-bone mineral metabolism disorder) guidelines for phosphorus control stipulate a serum phosphorus value of 3.5 to 6.0 mg/dL.

A serum phosphorus level of below 3.5 mg/dL is hypophosphatemia which is a cause of rachitis or osteomalacia, while a level of 6.0 mg/dL or higher is hyperphosphatemia, which can lead to cardiovascular calcification.

Alimentary therapy to lower phosphorus consumption also depends on the nutritional status of the patient, while the preferences of the patient must also be taken into account, and therefore management of body phosphorus concentrations with alimentary therapy can be difficult.

Some drug therapies exist that are oral phosphorus adsorbents that can bind with dietary phosphate ion in the gastrointestinal tract to form insoluble phosphates, and that are taken either before or during meals to inhibit absorption of phosphorus through the intestinal tract, thus managing phosphorus concentrations. However, a very large amount of phosphorus adsorbent must be taken before meals for such drug therapy. This results in a high probability of side-effects when a phosphorus adsorbent is taken, such as vomiting, feeling of fullness, constipation or drug buildup in the body, such that the compliance is extremely low (often said to be 50% or lower), and therefore management of phosphorus concentrations by drugs can be problematic for both doctors and patients.

PTL 1 discloses circulating a dialysis composition containing a phosphorus adsorbent in dialysate during hemodialysis treatment to efficiently remove phosphorus in blood without direct contact of the phosphorus adsorbent with the blood.

Also, PTL 2 discloses a hemodialysis system wherein a phosphorus adsorbent comprising a polycationic polymer is provided separately from the hemodialyzer, whereby phosphorus accumulated in the blood is removed through the route of blood outside the body.

PTL 3 discloses a porous molded body suited as an adsorbent that can rapidly remove phosphorus and other components by adsorption.

However, these blood purification devices of the prior art have low adsorption capacity for phosphorus, and have also been insufficient in terms of safe usability.

CITATION LIST

Patent Literature

[PTL 1] International Patent Publication No. WO2011/125758
[PTL 2] Japanese Unexamined Patent Publication No. 2002-102335
[PTL 3] Japanese Patent Publication No. 4671419

SUMMARY

Technical Problem

In light of these problems of the prior art, it is an object of the present invention to provide a blood purification device comprising a porous molded body, which has high phosphorus adsorption capacity and safe usability.

Solution to Problem

As a result of repeated experimentation with the aim of solving the problems described above, the present inventors have completed this invention upon finding that it is possible to provide a blood purification device having a high phosphorus clearance value and safe usability, by adding an inorganic ion adsorbent with high phosphorus adsorption capacity to a porous molded body, while washing with a supercritical fluid or subcritical fluid to completely remove the microparticles and trace metals generated by the blood purification device comprising the porous molded body.

Specifically, the present invention provides the following.

A blood purification device comprising a porous molded body that includes an inorganic ion adsorbent, wherein the concentrations of Mg, Al, Ti, V, Cr, Mn, Fe, Ni, Cu, Zn, Ga, Rb, Sr, Y, Zr, Mo, Ru, Ag, Cd, Sn, Cs, La, Pr, Sm, Gd, Tb, Ta, Au, Tl, Co, In and Bi are all 0.1 ppb or lower and the concentrations of Ba, Nd, Pb and Ce are all 1 ppb or lower, in physiological saline for injection in the blood purification device at 3 months and 6 months after opening the physiological saline for injection, while the number of microparticles with sizes of 10 μm or greater is no more than 25 and the number of microparticles with sizes of 25 μm or greater is no more than 3, in 1 mL of the physiological saline for injection at 3 months and 6 months after the same physiological saline for injection has been encapsulated in the blood purification device.

Advantageous Effects of Invention

The blood purification device of the invention has high phosphorus adsorption capacity and safe usability.

Specifically, the blood purification device of the invention has excellent selectivity and adsorption for phosphorus in blood even with a high blood flow rate during extracorporeal circulation treatment, and can eliminate the necessary amount of phosphorus from blood without affecting other components in the blood. Moreover, because phosphorus in blood can be effectively removed by extracorporeal circulation, phosphorous levels in blood can be properly managed without taking oral phosphorus adsorbents that produce side-effects.

By using the blood purification device of the invention, phosphorus levels in the blood of a dialysis patient can be properly managed without taking oral phosphorus adsorbents, or by taking only small amounts (auxiliary usage), thus avoiding side-effects in dialysis patients.

DESCRIPTION OF EMBODIMENTS

Figure 1:
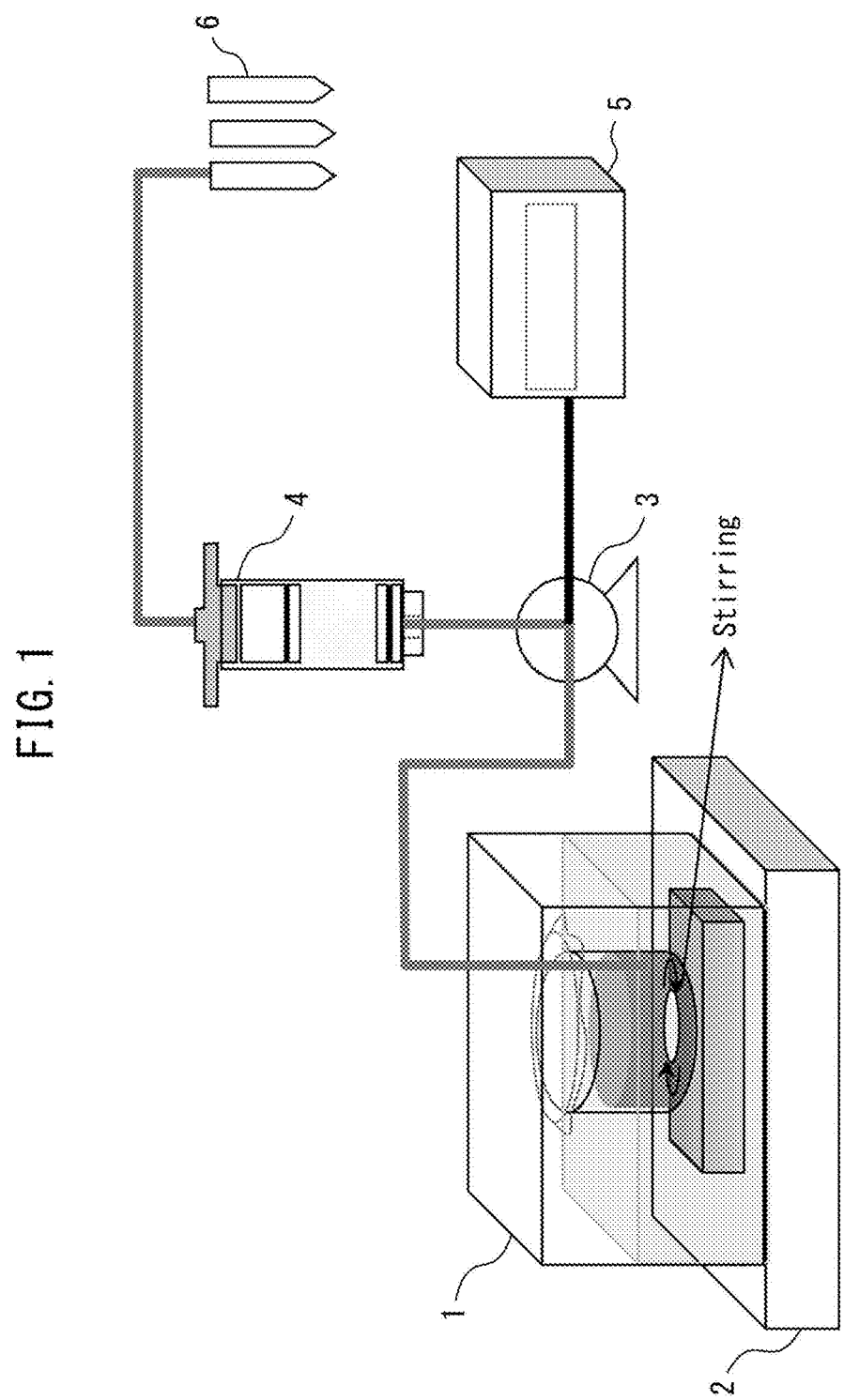
FIG. 1 is an overview diagram of a column flow test apparatus in a blood purification device according to an embodiment, with low-phosphorus serum using bovine plasma.

Embodiments of the invention will now be explained in detail.

The blood purification device of the embodiment is a blood purification device comprising a porous molded body that includes an inorganic ion adsorbent, wherein the concentrations of Mg, Al, Ti, V, Cr, Mn, Fe, Ni, Cu, Zn, Ga, Rb, Sr, Y, Zr, Mo, Ru, Ag, Cd, Sn, Cs, La, Pr, Sm, Gd, Tb, Ta, Au, Tl, Co, In and Bi are all 0.1 ppb or lower and the concentrations of Ba, Nd, Pb and Ce are all 1 ppb or lower, in physiological saline for injection in the blood purification device at 3 months and 6 months after opening the physiological saline for injection, while the number of microparticles with sizes of 10 μm or greater is no more than 25 and the number of microparticles with sizes of 25 μm or greater is no more than 3, in 1 mL of the physiological saline for injection at 3 months and 6 months after the same physiological saline for injection has been encapsulated in the blood purification device.

For safe usability, production of the blood purification device of the embodiment must ensure that the concentrations of Mg, Al, Ti, V, Cr, Mn, Fe, Ni, Cu, Zn, Ga, Rb, Sr, Y, Zr, Mo, Ru, Ag, Cd, Sn, Cs, La, Pr, Sm, Gd, Tb, Ta, Au, Tl, Co, In and Bi are all 0.1 ppb or lower and the concentrations of Ba, Nd and Pb are all 1 ppb or lower in the saline solution at 3 months and 6 months after the physiological saline for injection has been encapsulated in the blood purification device. The metal concentration in the saline solution at 3 months and 6 months afterwards is the difference compared to the metal concentration in the physiological saline for injection before injection into the blood purification device.

[Porous Molded Body]

The porous molded body of the embodiment contains an inorganic ion adsorbent, and preferably it is composed of a porous molded body-forming polymer, the inorganic ion adsorbent and an inorganic ion adsorbent. In the porous molded body, the sum of the pore volumes for pore diameters of 1 nm to 80 nm as measured by the nitrogen gas adsorption method is preferably 0.05 $cm^3/g$ to 0.7 $cm^3/g$ per unit mass of the inorganic ion adsorbent.

For this embodiment, the sum of the pore volumes for pore diameters of 1 nm to 80 nm measured by the nitrogen gas adsorption method is 0.05 $cm^3/g$ to 0.7 $cm^3/g$, preferably 0.1 $cm^3/g$ to 0.6 $cm^3/g$ and more preferably 0.2 $cm^3/g$ to 0.5 $cm^3/g$ per unit mass of the inorganic ion adsorbent.

The pore volume is obtained by measuring the freeze-dried porous molded body by the nitrogen gas adsorption method and calculating by the BJH method.

The sum Va of the pore volumes per unit mass of the inorganic ion adsorbent is determined by the following formula (7):

$$Va = Vb/Sa \times 100 \qquad (7)$$

where Vb ($cm^3/g$) is the pore volume per unit mass of the porous molded body calculated for the dried porous molded body and Sa (mass %) is the loading mass of the inorganic ion adsorbent in the porous molded body.

The loading mass (mass %) Sa of the inorganic ion adsorbent in the porous molded body is determined by the following formula (8):

$$Sa = Wb/Wa \times 100 \qquad (8)$$

where Wa (g) is the mass of the porous molded body when dry and Wb (g) is the ash content mass.

The ash content is the portion remaining after the porous molded body has been fired at 800° C. for 2 hours.

Since the pore volume of the porous molded body measured by the nitrogen gas adsorption method is a value primarily reflecting the pore volume of the inorganic ion adsorbent in the porous molded body, a larger value represents higher diffusion efficiency of ions into the inorganic ion adsorbent, and higher adsorption capacity.

If the sum of the pore volumes per unit mass of the inorganic ion adsorbent is smaller than 0.05 $cm^3/g$, the pore volume of the inorganic ion adsorbent will be reduced and the adsorption capacity will be significantly lower. If the value is higher than 0.7 $cm^3/g$, on the other hand, the bulk density of the inorganic ion adsorbent will increase and the viscosity of the stock solution slurry will increase, thereby hampering granulation.

For the embodiment, the area-to-weight ratio of the porous molded body measured by the nitrogen gas adsorption method is preferably 50 m$^2$/g to 400 m$^2$/g, more preferably 70 m$^2$/g to 350 m$^2$/g and even more preferably 100 m$^2$/g to 300 m$^2$/g.

The area-to-weight ratio is obtained by measuring the freeze-dried porous molded body by the nitrogen gas adsorption method and calculating by the BET method.

Since the area-to-weight ratio of the porous molded body measured by the nitrogen gas adsorption method is a value primarily reflecting the area-to-weight ratio of the inorganic ion adsorbent in the porous molded body, a larger value represents a greater number of ion adsorption sites and higher adsorption capacity.

If the area-to-weight ratio of the porous molded body is smaller than 50 m$^2$/g, the number of adsorption sites of the inorganic ion adsorbent will be lower and the adsorption capacity will be significantly reduced. If the value is higher than 400 m$^2$/g, on the other hand, the bulk density of the inorganic ion adsorbent will increase and the viscosity of the stock solution slurry will increase, thereby hampering granulation.

For the embodiment, the loading mass of the inorganic ion adsorbent in the porous molded body is preferably 30 mass % to 95 mass %, more preferably 40 mass % to 90 mass % and even more preferably 50 mass % to 80 mass %.

If the loading mass is less than 30 mass %, the contact frequency between the ions to be adsorbed and the inorganic ion adsorbent as the adsorption substrate will tend to be insufficient, while if it is greater than 95 mass %, the strength of the porous molded body will tend to be lacking.

The porous molded body of the embodiment preferably has a mean particle size of 100 µm to 2500 µm and is essentially in the form of spherical particles, the mean particle size being preferably 150 µm to 2000 µm, more preferably 200 µm to 1500 µm and even more preferably 300 µm to 1000 µm.

The porous molded body of the embodiment is preferably in the form of spherical particles, although the spherical particles are not limited to being merely spherical and may also be elliptical spherical.

The mean particle size for the embodiment is the median diameter of the sphere-equivalent size determined from the angular distribution of the intensity of scattered light due to laser light diffraction, assuming the porous molded body to be spherical.

If the mean particle size is 100 µm or greater, pressure loss will be low when the porous molded body is packed into a container such as a column or tank, making it suitable for high-speed water treatment. If the mean particle size is 2500 µm or smaller, on the other hand, the surface area of the porous molded body can be increased when it has been packed into a column or tank, allowing reliable adsorption of ions even with high-speed liquid flow treatment.

[Inorganic Ion Adsorbent]

The inorganic ion adsorbent contained in or composing the porous molded body of the embodiment is an inorganic substance that exhibits an ion adsorption phenomenon or ion-exchange phenomenon.

Examples of natural inorganic ion adsorbents include mineral substances such as zeolite and montmorillonite.

Specific examples of mineral substances include kaolin minerals having a single layer lattice with aluminosilicates, muscovite, glauconite, kanuma soil, pyrophyllite and talc having a 2-layer lattice structure, and feldspar, zeolite and montmorillonite having a three-dimensional frame structure.

Examples of synthetic-based inorganic ion adsorbents include metal oxides, polyvalent metal salts and insoluble hydrous oxides. Metal oxides include complex metal oxides, composite metal hydroxides and metal hydrous oxides.

From the viewpoint of adsorption performance for the target of adsorption, and especially phosphorus, the inorganic ion adsorbent preferably contains at least one metal oxide represented by the following formula (1):

{where x is 0 to 3, n is 1 to 4, m is 0 to 6, and M and N are metal elements selected from the group consisting of Ti, Zr, Sn, Sc, Y, La, Ce, Pr, Nd, Sm, Eu, Gd, Tb, Dy, Ho, Er, Tm, Yb, Lu, Al, Si, Cr, Co, Ga, Fe, Mn, Ni, V, Ge, Nb and Ta, and are different from each other}.

The metal oxide may be a non-water-containing (non-hydrated) metal oxide where m in formula (1) is 0, or it may be a water-containing metal oxide (hydrated metal oxide) wherein m is a numerical value other than 0.

A metal oxide where x in formula (1) is a numerical value other than 0 is a complex metal oxide represented by the chemical formula in which each metal element is evenly distributed in a regular manner throughout all of the oxides, and the compositional ratio of the metal elements in the metal oxide is constant.

Specific ones include nickel ferrite (NiFe$_2$O$_4$) or hydrous ferrite of zirconium (Zr·Fe$_2$O$_4$·mH$_2$O, where m is 0.5 to 6), which form a perovskite structure or spinel structure.

The inorganic ion adsorbent may also contain more than one type of metal oxide represented by formula (1).

From the viewpoint of excellent adsorption performance for components to be adsorbed, and especially phosphorus, a metal oxide as the inorganic ion adsorbent is preferably selected from among the following groups (a) to (c):

(a) hydrated titanium oxide, hydrated zirconium oxide, hydrated tin oxide, hydrated cerium oxide, hydrated lanthanum oxide and hydrated yttrium oxide, (b) complex metal oxides comprising at least one metal element selected from the group consisting of titanium, zirconium, tin, cerium, lanthanum, neodymium and yttrium and at least one metal element selected from the group consisting of aluminum, silicon and iron, and (c) activated alumina.

It may be a material selected from among any of groups (a) to (c), or materials selected from among any of groups (a) to (c) may be used in combination, or materials of each of groups (a) to (c) may be used in combination. When materials are used in combination, they may be a mixture of two or more materials selected from among any of groups (a) to (c), or they may be a mixture of two or more materials selected from among two or more of groups (a) to (c).

From the viewpoint of low cost and high adsorption properties, the inorganic ion adsorbent may contain aluminum sulfate-added activated alumina.

From the viewpoint of inorganic ion adsorption properties and production cost, the inorganic ion adsorbent is more preferably one having a metal element other than M and N in solid solution in addition to the metal oxide represented by formula (1).

For example, it may be one with iron in solid solution with hydrated zirconium oxide represented by ZrO$_2$·mH$_2$O (where m is a numerical value other than 0).

Examples of salts of polyvalent metals include hydrotalcite-based compounds represented by the following formula (2):

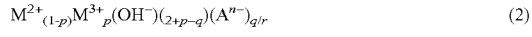

{where $M^{2+}$ is at least one divalent metal ion selected from the group consisting of $Mg^{2+}$, $Ni^{2+}$, $Zn^{2+}$, $Fe^{2+}$, $Ca^{2+}$ and $Cu^{2+}$, $M^{3+}$ is at least one trivalent metal ion selected from the group consisting of $Al^{3+}$ and $Fe^{3+}$, $A^{n-}$ is an n-valent anion, $0.1 \leq p \leq 0.5$, $0.1 \leq q \leq 0.5$, and r is 1 or 2}.

A hydrotalcite-based compound represented by formula (2) is preferred because it is inexpensive as an inorganic ion adsorbent and has high adsorption properties.

Examples of insoluble hydrous oxides include insoluble heteropolyacid salts and insoluble hexacyanoferrates.

Metal carbonates have excellent performance from the standpoint of adsorption properties, but from the standpoint of elution, the purpose of use must be considered when carbonates are to be used as inorganic ion adsorbents.

From the viewpoint of allowing ion-exchange reaction with the carbonate ion, the metal carbonate may include at least one type of metal carbonate represented by the following formula (3):

$$Q_yR_z(CO_3)_s \cdot tH_2O \qquad (3)$$

{where y is 1 or 2, Z is 0 or 1, s is 1 to 3, t is 0 to 8, and Q and R are metal elements selected from the group consisting of Mg, Ca, Sr, Ba, Sc, Mn, Fe, Co, Ni, Ag, Zn, Y, La, Ce, Pr, Nd, Sm, Eu, Gd, Tb, Dy, Ho, Er, Tm, Yb and Lu and are different from each other}.

The metal carbonate may be a non-water-containing (non-hydrated) metal carbonate where tin formula (3) is 0, or it may be a hydrate where t is a numerical value other than 0.

From the viewpoint of low elution and excellent adsorption properties for phosphorus, boron, fluorine and/or arsenic, the inorganic ion adsorbent is preferably selected from among the following group (d):

(d) magnesium carbonate, calcium carbonate, strontium carbonate, barium carbonate, scandium carbonate, manganese carbonate, iron carbonate, cobalt carbonate, nickel carbonate, silver carbonate, zinc carbonate, yttrium carbonate, lanthanum carbonate, cerium carbonate, praseodymium carbonate, neodymium carbonate, samarium carbonate, europium carbonate, gadolinium carbonate, terbium carbonate, dysprosium carbonate, holmium carbonate, erbium carbonate, thulium carbonate, ytterbium carbonate and lutetium carbonate.

Because elution of the metal carbonate or recrystallization of inorganic ions and metal ions on the metal carbonate are expected as mechanisms of adsorption of inorganic ions by the metal carbonate, a metal carbonate with higher solubility is expected to have higher inorganic ion adsorption and more excellent adsorption performance. Metal elution from the inorganic ion adsorbent is also a concern, and therefore careful study is necessary for uses where metal elution may be problem.

The inorganic ion adsorbent composing the porous molded body of the embodiment may also contain contaminating impurity elements that are present due to the production process, in ranges that do not interfere with functioning of the porous molded body. Examples of potentially contaminating impurity elements include nitrogen (in the form of nitric acid, nitrous acid or ammonium), sodium, magnesium, sulfur, chlorine, potassium, calcium, copper, zinc, bromine, barium and hafnium.

The inorganic ion adsorbent composing the porous molded body of the embodiment may also contain contaminating impurity elements that are present due to the production process, in ranges that do not interfere with functioning of the porous molded body. Examples of potentially contaminating impurity elements include nitrogen (in the form of nitric acid, nitrous acid or ammonium), sodium, magnesium, sulfur, chlorine, potassium, calcium, copper, zinc, bromine, barium and hafnium.

The method of replacement to organic liquid is not particularly restricted, and it may be centrifugal separation and filtration after dispersing the water-containing inorganic ion adsorbent in an organic liquid, or passage of an organic liquid after filtration with a filter press. For a higher replacement rate, it is preferred to repeat a method of filtration after dispersion of the inorganic ion adsorbent in an organic liquid.

The replacement rate of water to organic liquid during production may be 50 mass % to 100 mass %, preferably 70 mass % to 100 mass % and more preferably 80 mass % to 100 mass %.

The organic liquid replacement rate is the value represented by the following formula (4):

$$Sb = 100 - Wc \qquad (4)$$

where Sb (mass %) is the replacement rate to organic liquid and Wc (mass %) is the moisture content of the filtrate after treating the water-containing inorganic ion adsorbent with the organic liquid.

The moisture content of the filtrate after treatment with the organic liquid can be determined by measurement by the Karl Fischer method.

Drying after replacement of the water in the inorganic ion adsorbent with organic liquid can inhibit aggregation during drying, can increase the pore volume of the inorganic ion adsorbent and can increase the adsorption capacity.

If the replacement rate of the organic liquid is less than 50 mass %, the aggregation suppressing effect during drying will be reduced and the pore volume of the inorganic ion adsorbent will not increase.

[Removal of Microparticles]

The blood purification device of the embodiment can be safely used even though the porous molded body contains an inorganic ion adsorbent. Specifically, the concentrations of Mg, Al, Ti, V, Cr, Mn, Fe, Ni, Cu, Zn, Ga, Rb, Sr, Y, Zr, Mo, Ru, Ag, Cd, Sn, Cs, La, Pr, Sm, Gd, Tb, Ta, Au, Tl, Co, In and Bi are all 0.1 ppb or lower and the concentration of Ba, Nd and Pb is 1 ppb or lower, in the saline solution at 3 months and 6 months after the physiological saline for injection has been encapsulated in the blood purification device. The blood purification device of the embodiment conforms to the approval standards for artificial kidney devices established by the Ministry of Health, Labour and Welfare, described below. Specifically, in the blood purification device of the embodiment, the number of microparticles with sizes of 10 µm or greater is no more than 25 and the number of microparticles with sizes of 25 µm or greater is no more than 3, in 1 mL of the physiological saline for injection at 3 months and 6 months after the physiological saline for injection has been encapsulated in the blood purification device, while the absorbance of an eluate test solution is 0.1 or lower, and the test solution does not contain a membrane pore retainer.

The present inventors have found that even though the porous molded body contains an inorganic ion adsorbent when the blood purification device of the embodiment is produced, microparticles generated by the blood purification device can be completely removed if it is washed with a supercritical fluid or subcritical fluid.

A supercritical fluid is a fluid in a state above the critical pressure (hereunder also referred to as "Pc") and above the critical temperature (hereunder also referred to as "Tc"). A subcritical fluid is a fluid in a state other than a supercritical state, with conditions of $0.5 < P/Pc < 1.0$ and $0.5 < T/Tc$, or 0.5<P/Pc and 0.5<T/Tc<1.0, where the pressure and temperature during reaction are denoted by P and T, respectively. The preferred ranges for the pressure and temperature of the subcritical fluid are 0.6<P/Pc<1.0 and 0.6<T/Tc, or 0.6<P/Pc and 0.6<T/Tc<1.0. When the fluid is water, the ranges for the temperature and pressure for a subcritical fluid may be 0.5<P/Pc<1.0 and 0.5<T/Tc, or 0.5<P/Pc and 0.5<T/Tc<1.0. The temperature is represented as degrees Celsius, but the formula representing the subcritical state does not apply if either Tc or T is a negative value.

The supercritical fluid or subcritical fluid used may be water or an organic medium such as alcohol, or a gas such as carbon dioxide, nitrogen, oxygen, helium, argon or air, or a mixed fluid comprising them. Carbon dioxide is most preferred because it allows a supercritical state to be achieved at nearly ordinary temperature, so that various different substances can be thoroughly dissolved.

[Porous Molded Body-Forming Polymer]

A porous molded body-forming polymer capable of forming a porous molded body to be used in the blood purification device of the embodiment may be any polymer capable of forming a porous molded body, examples of which include various types such as polysulfone-based polymers, polyvinylidene fluoride-based polymers, polyvinylidene chloride-based polymers, acrylonitrile-based polymers, polymethyl methacrylate-based polymers, polyamide-based polymers, polyimide-based polymers, cellulosic polymers, ethylene-vinyl alcohol copolymer-based polymers, polyaryl ether sulfones, polypropylene-based polymers, polystyrene-based polymers and polycarbonate-based polymers. Among these, aromatic polysulfones are preferred for excellent thermostability, acid resistance, alkali resistance and mechanical strength.

Aromatic polysulfones to be used for the embodiment include those having repeating units represented by the following formula (5):

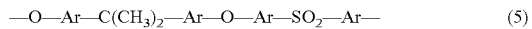

—O—Ar—C(CH$_3$)$_2$—Ar—O—Ar—SO$_2$—Ar—  (5)

{where Ar is a disubstituted phenyl group at the para position} or the following formula (6):

—O—Ar—SO$_2$—Ar—  (6)

{where Ar is a disubstituted phenyl group at the para position}. The polymerization degree and molecular weight of the aromatic polysulfone are not particularly restricted.

[Hydrophilic Polymer]

A hydrophilic polymer used to form the porous molded body of the embodiment is not particularly restricted so long as it is a biocompatible polymer that swells but does not dissolve in water, and examples include polymers having one or more sulfonic acid, carboxyl, carbonyl, ester, amino, amide, cyano, hydroxyl, methoxy, phosphate, oxyethylene, imino, imide, iminoether, pyridine, pyrrolidone, imidazole or quaternary ammonium groups.

When the porous molded body-forming polymer is an aromatic polysulfone, a polyvinylpyrrolidone (hereunder also referred to as "PVP")-based polymer is most preferred as the hydrophilic polymer.

Polyvinylpyrrolidone-based polymers include vinylpyrrolidone-vinyl acetate copolymer, vinylpyrrolidone-vinylcaprolactam copolymer and vinylpyrrolidone-vinyl alcohol copolymer, and preferably at least one of these is used. From the viewpoint of compatibility with the polysulfone-based polymer, the most suitable ones for use are polyvinylpyrrolidone, vinylpyrrolidone-vinyl acetate copolymer and vinylpyrrolidone-vinylcaprolactam copolymer.

The porous molded body to be used in the blood purification device of the embodiment is preferably coated with a biocompatible polymer, the biocompatible polymer preferably being selected from the group consisting of polymethoxyethyl acrylate (PMEA) and polyvinylpyrrolidone (PVP)-based polymers.

[Polymethoxyethyl Acrylate (PMEA)]

The biocompatibility (blood compatibility) of PMEA is described in detail in "Artificial organ surface-biocompatibilizing materials", Tanaka, K., BIO INDUSTRY, Vol 20, No. 12, 59-70 2003.

This article describes preparing PMEA, and an acrylate-based polymer with a different side chain structure for comparison, and evaluating platelets, leukocytes, complement and coagulation markers during circulation of blood, and it is stated that "the PMEA surface had minor activation of blood components compared to other polymers, while the PMEA surface had excellent blood compatibility due to a significantly low level of human platelet adhesion and low morphological changes in the adhered platelets".

Presumably, therefore, PMEA has good blood compatibility not simply because it is hydrophilic due to ester groups in the structure, but rather the state of water molecules adsorbed onto the surface also has a major effect on its blood compatibility.

It is known that in the ATR-IR method, waves impinging on a sample are reflected after entering into the sample to a small degree, such that infrared absorption in the region of the entering depth can be measured, but the present inventors have found that the region of measurement in the ATR-IR method is essentially equal to the depth of the "surface layer" that corresponds to the surface of the porous molded body. That is, it was found that the blood compatibility in a region at approximately equal depth as the ATR-IR measurement region governs the blood compatibility of the porous molded body, and that the presence of PMEA in that region can provide a blood purification device with consistent blood compatibility. If the surface of the porous molded body is coated with PMEA, then generation of microparticles from the blood purification device after long-term storage can also be inhibited.

The measuring region by ATR-IR depends on the wavelength and incident angle of infrared light in air, the refractive index of the prism and the refractive index of the sample, but it will usually be a region of within 1 μm from the surface.

The presence of PMEA on the surface of the porous molded body can be confirmed by thermal decomposition gas chromatography-mass spectrometry of the porous molded body. The presence of PMEA is estimated using the peak near 1735 cm$^{-1}$ on the infrared absorption curve from total reflection infrared absorption (ATR-IR) measurement of the surface of the porous molded body, although neighboring peaks can arise due to other substances. Thermal decomposition gas chromatography-mass spectrometry may therefore be performed to confirm the presence of PMEA, by confirming PMEA-derived 2-methoxyethanol.

PMEA has a characteristic solubility in solvents. For example, PMEA does not dissolve in a 100% ethanol solvent but has a range of solubility in a water/ethanol mixed solvent, depending on the mixing ratio. If the mixing ratio is in the soluble range, the peak intensity of the PMEA-attributed peak (near 1735 cm$^{-1}$) is higher with a larger amount of water.

For a porous molded body comprising PMEA on the surface, the variation in water permeability is minimal and product design is simpler, due to lower variation in pore sizes on the surface. The porous molded body of this embodiment has PMEA on the surface, but when the PMEA has been coated onto the porous molded body it is assumed that the PMEA adheres as an ultra-thin film, coating the porous molded body surface essentially without blocking the pores. PMEA is especially preferred because of its small molecular weight and short molecular chains, which makes it less likely to form a thick coating film structure or to alter the structure of the porous molded body. PMEA is also preferred because it has high compatibility with other substances, allowing it to be evenly coated onto the porous molded body surface and helping to improve the blood compatibility.

The weight-average molecular weight of the PMEA can be measured by gel permeation chromatography (GPC), for example.

The method of forming a PMEA coating layer on the surface of the porous molded body may be a method of coating by flowing a PMEA-dissolved coating solution from the top of a column (vessel) packed with the porous molded body.

[Polyvinylpyrrolidone (PVP)-Based Polymer]

The polyvinylpyrrolidone (PVP)-based polymer is not particularly restricted, but polyvinylpyrrolidone (PVP) is suitable for use.

[Number of Microparticles, Eluted Metal Concentration]

A blood purification device that is to be applied for dialysis must conform to the approval standards for artificial kidney devices established by the Ministry of Health, Labour and Welfare, in order to obtain approval for production as a dialysis-type (afferent) artificial kidney device. The blood purification device of the embodiment must therefore conform to the eluting material test criteria listed in the approval standards for artificial kidney devices. In the blood purification device of the embodiment, the number of microparticles with sizes of 10 μm or greater is no more than 25 in 1 mL of saline solution and the number of microparticles with sizes of 25 μm or greater is no more than 3 in 1 mL of saline solution, at 3 months and 6 months after the physiological saline for injection has been encapsulated in the blood purification device, while the absorbance of the eluate test solution is 0.1 or lower.

For the same reason, in the blood purification device of the embodiment, the concentrations of Mg, Al, Ti, V, Cr, Mn, Fe, Ni, Cu, Zn, Ga, Rb, Sr, Y, Zr, Mo, Ru, Ag, Cd, Sn, Cs, La, Pr, Sm, Gd, Tb, Ta, Au, Tl, Co, In and Bi are all 0.1 ppb or lower and the concentration of Ba, Nd, Pb and Ce is 1 ppb or lower, in the saline solution at 3 months and 6 months after the physiological saline for injection has been encapsulated in the blood purification device.

The measuring methods for the number of microparticles and Mg, Al, Ti, V, Cr, Mn, Fe, Ni, Cu, Zn, Ga, Rb, Sr, Y, Zr, Mo, Ru, Ag, Cd, Sn, Cs, La, Pr, Sm, Gd, Tb, Ta, Au, Tl, Co, In, Bi, Ba, Nd, Pb and Ce in the physiological saline for injection encapsulated in the blood purification device are as follows.

(1) Measuring Method for Wet-Type Blood Purification Device

A wet-type blood purification device encapsulates a solution (such as UF filtration membrane water) just before shipping and is subjected to radiation sterilization in the solution and then shipped. In a wet-type blood purification device, after the solution has been completely removed and after the porous molded body in the blood purification device has been flushed with 10 L of physiological saline for injection (or after filtering from the membrane inner surface side to the membrane outer surface side if the porous molded body is a hollow fiber membrane), fresh physiological saline for injection is encapsulated, and then the mixture is incubated at 25° C.±1° C. and stored in a stationary state for 3 months. Sampling of the saline solution from the blood purification device is carried out after removing as much of the solution (filled solution) as possible from the blood purification device and then uniformly mixing. For example, after sampling for measurement at 3 months, the remaining saline solution is placed in the original blood purification device and sealed, stored for an additional 3 months, and used for measurement at 6 months.

(2) Measuring Method for Dry-Type Blood Purification Device

Radiation sterilization is usually not carried out in solution with a dry-type blood purification device, and it is usually shipped in a dry state. After the porous molded body in the blood purification device has been flushed with 10 L of physiological saline for injection (or after filtering from the membrane inner surface side to the membrane outer surface side if the porous molded body is a hollow fiber membrane), fresh physiological saline for injection is encapsulated, and then the mixture is incubated at 25° C.±1° C. and stored in a stationary state for 3 months. Sampling of the saline solution from the blood purification device is carried out after removing as much of the solution (filled solution) as possible from the blood purification device and then uniformly mixing. For example, after sampling for measurement at 3 months, the remaining saline solution is placed in the original blood purification device and sealed, stored for an additional 3 months, and used for measurement at 6 months.

The number of microparticles in the sampled solution (or filled solution) can be measured with a particle counter.

[Phosphorus Adsorption Performance of Porous Molded Body]

The porous molded body of the embodiment can be suitably used for adsorption of phosphorus during hemodialysis of a dialysis patient. The composition of blood is categorized into blood plasma components and blood cell components, with the blood plasma components comprising 91% water, 7% proteins, and lipid components and inorganic salts, and with phosphorus in the blood being present as phosphate ions among the blood plasma components. The blood cell components are composed of 96% erythrocytes, 3% leukocytes and 1% platelets, the sizes of erythrocytes being 7 to 8 μm in diameter, the sizes of leukocytes being 5 to 20 μm in diameter and the sizes of platelets being 2 to 3 μm in diameter.

Since the most common pore size of a porous molded body measured by a mercury porosimeter is 0.08 to 0.70 μm, and consequently the abundance of the inorganic ion adsorbent on the outer surface is high, this allows phosphorus ions to be reliably adsorbed even by high-speed liquid flow treatment, and also allows excellent penetration, diffusion and adsorption of phosphorus ions into the porous molded body. There is also no reduction in blood flow by clogging with blood cell components.

For this embodiment, the surface of the porous molded body has a biocompatible polymer, allowing it to be used as a more suitable phosphorus adsorbent for blood treatment.

If the device comprises a porous molded body with the most common pore size being 0.08 to 0.70 μm and the surface of the porous molded body has a biocompatible polymer, then phosphorus ions in blood will be selectively and reliably adsorbed, so that the phosphorus concentration in blood returning to the body will be nearly 0. By returning essentially phosphorus-free blood to the body, presumably phosphorus will more actively move into the blood from intracellular or extracellular regions, for a greater refilling effect.

By inducing a refilling effect that supplements phosphorus in the blood, it may even be possible to eliminate phosphorus present in extracellular fluid or in cells, which normally cannot be eliminated.

Thus, phosphorus levels in the blood of a dialysis patient can be properly managed without taking oral phosphorus adsorbents, or by taking only small amounts (auxiliary usage), thus avoiding side-effects in dialysis patients.

A blood purification device having a porous molded body packed into a vessel (column) may be used during dialysis in connection with a dialyzer, either in series before and after or in parallel with it. The blood purification device of the embodiment can be used as a blood purification device for adsorption of phosphorus, and has excellent selectivity and adsorption performance for inorganic phosphorus even with a low phosphorus level in the blood and a high space velocity.

From the viewpoint of helping to induce a refilling effect, preferably the blood purification device of the embodiment is used in connection before and after the dialyzer.

From the viewpoint of allowing a refilling effect to be obtained, the phosphorus adsorption rate (%) (the proportion of blood phosphorus that is absorbed) is preferably 50% or higher, more preferably 60% or higher, and most suitably 70% or higher, 80% or higher, 85% or higher, 90% or higher, 95% or higher or 99% or higher.

There are no limitations on the material of the vessel (column) of the blood purification device of the embodiment, and examples are mixed resins such as polystyrene-based polymers, polysulfone-based polymers, polyethylene-based polymers, polypropylene-based polymers, polycarbonate-based polymers and styrene-butadiene blocked copolymers. A polyethylene-based polymer or polypropylene-based polymer is preferably used from the viewpoint of material cost.

[Method for Producing Porous Molded Body]

The method for producing a porous molded body of the embodiment will now be described in detail.

The method for producing a porous molded body of the embodiment includes, for example, (1) a step of drying an inorganic ion adsorbent, (2) a step of pulverizing the inorganic ion adsorbent obtained in step (1), (3) a step of mixing the inorganic ion adsorbent obtained in step (2), a good solvent for the porous molded body-forming polymer, a porous molded body-forming polymer and, depending on the case, a hydrophilic polymer (water-soluble polymer) to prepare a slurry, (4) a step of molding the slurry obtained in step (3), and (5) a step of coagulating the molded article obtained in step (4) in a poor solvent.

[Step (1): Inorganic Ion Adsorbent Drying Step]

In step (1), the inorganic ion adsorbent is dried to obtain a powder. In order to inhibit aggregation during the drying, preferably the drying during production is carried out after replacing the moisture with an organic liquid. The organic liquid is not particularly restricted so long as it has an effect of inhibiting aggregation of the inorganic ion adsorbent, but it is preferred to use a liquid with high hydrophilicity. Examples include alcohols, ketones, esters and ethers.

The replacement rate to the organic liquid may be 50 mass % to 100 mass %, preferably 70 mass % to 100 mass % and more preferably 80 mass % to 100 mass %.

The method of replacement to organic liquid is not particularly restricted, and it may be centrifugal separation and filtration after dispersing the water-containing inorganic ion adsorbent in an organic liquid, or passage of an organic liquid after filtration with a filter press. For a higher replacement rate, it is preferred to repeat a method of filtration after dispersion of the inorganic ion adsorbent in an organic liquid.

The replacement rate to the organic liquid can be determined by measurement of the filtrate moisture content by the Karl Fischer method.

Drying after replacement of the water in the inorganic ion adsorbent with organic liquid can inhibit aggregation during drying, can increase the pore volume of the inorganic ion adsorbent and can increase the adsorption capacity.

If the replacement rate of the organic liquid is less than 50 mass %, the aggregation suppressing effect during drying will be reduced and the pore volume of the inorganic ion adsorbent will not increase.

[Step (2): Inorganic Ion Adsorbent Pulverizing Step]

In step (2), the inorganic ion adsorbent powder obtained from step (1) is pulverized. The pulverizing method is not particularly restricted, and may be dry grinding or wet grinding.

A dry grinding method is not particularly restricted, and it may be one employing an impact crusher such as a hammer mill, an airflow pulverizer such as a jet mill, a medium pulverizer such as a ball mill or a compression pulverizer such as a roller mill.

An airflow pulverizer is preferred among these because it can create a sharp particle size distribution of the pulverized inorganic ion adsorbent.

A wet grinding method is not particularly restricted so long as it allows pulverizing and mixing together of the inorganic ion adsorbent and the good solvent for the porous molded body-forming polymer, and it may employ means used in physical pulverizing methods such as pressurized disruption, mechanical grinding or ultrasonic treatment.

Specific examples of pulverizing and mixing means include blenders such as generator shaft homogenizers and Waring blenders, medium agitation mills such as sand mills, ball mills, attritors and bead mills, and jet mills, mortar/pestle combinations, kneaders and sonicators.

A medium agitation mill is preferred for high pulverizing efficiency and to allow pulverizing to a highly viscous state.

The ball diameter used in a medium agitation mill is not particularly restricted but is preferably 0.1 mm to 10 mm. If the ball diameter is 0.1 mm or greater, the ball mass will be sufficient to provide pulverizing force and high pulverizing efficiency, while a ball diameter of 10 mm or smaller will result in excellent fine pulverizing power.

The material of the ball used in a medium agitation mill is not particularly restricted, and it may be a metal such as iron or stainless steel, or a ceramic which is an oxide such as alumina or zirconia or a non-oxide such as silicon nitride or silicon carbide. Zirconia is superior among these for its excellent abrasion resistance, and from the viewpoint of low contamination (wear contamination) into products.

After pulverizing, a filter or the like is preferably used for filtration purification with the inorganic ion adsorbent in a fully dispersed state in the good solvent for the porous molded body-forming polymer.

The particle size of the pulverized and purified inorganic ion adsorbent is 0.001 to 10 μm, preferably 0.001 to 2 μm and more preferably 0.01 to 0.1 μm. A smaller particle size is more favorable for uniformly dispersing the inorganic ion adsorbent in the membrane-forming solution. It tends to be difficult to produce uniform microparticles with sizes of smaller than 0.001 μm. With an inorganic ion adsorbent exceeding 10 μm, it tends to be difficult to stably produce a porous molded body.

[Step (3): Slurry Preparation Step]

In step (3), the inorganic ion adsorbent obtained in step (2), a good solvent for the porous molded body-forming polymer, a porous molded body-forming polymer and, depending on the case, a water-soluble polymer (hydrophilic polymer) are mixed to prepare a slurry.

The good solvent for the porous molded body-forming polymer used in step (2) and step (3) is not particularly restricted so long as it stably dissolves the porous molded body-forming polymer at greater than 1 mass % under the production conditions for the porous molded body, and any conventionally known one may be used.

Examples of good solvents include N-methyl-2-pyrrolidone (NMP), N,N-dimethylacetamide (DMAC) and N,N-dimethylformamide (DMF).

The good solvent used may be a single one alone, or two or more may be used in admixture.

The amount of porous molded body-forming polymer added in step (3) may be such that the proportion of porous molded body-forming polymer/(porous molded body-forming polymer+water-soluble polymer+good solvent for porous molded body-forming polymer) is preferably 3 mass % to 40 mass % and more preferably 4 mass % to 30 mass %. If the porous molded body-forming polymer content is 3 mass % or greater a porous molded body with high strength can be obtained, and if it is 40 mass % or lower a porous molded body with high porosity can be obtained.

While addition of a water-soluble polymer is not absolutely necessary in step (3), addition can yield a homogeneous porous molded body comprising a filamentous structure that forms a three-dimensional connected network structure on the outer surface and interior of the porous molded body, or in other words, a porous molded body can be obtained with easier pore size control and reliable ion adsorption even with high-speed liquid flow treatment.

The water-soluble polymer used in step (3) is not particularly restricted so long as it is compatible with the good solvent for the porous molded body-forming polymer, and with the porous molded body-forming polymer.

A natural polymer, semisynthetic polymer or synthetic polymer may be used as the water-soluble polymer.

Examples of natural polymers include guar gum, locust bean gum, carrageenan, gum arabic, tragacanth, pectin, starch, dextrin, gelatin, casein and collagen.

Examples of semisynthetic polymers include methyl cellulose, ethyl cellulose, hydroxyethyl cellulose, ethylhydroxyethyl cellulose, carboxymethyl starch and methyl starch.

Examples of synthetic polymers include polyvinyl alcohol, polyvinylpyrrolidone (PVP), polyvinyl methyl ether, carboxyvinyl polymer, sodium polyacrylate, and polyethylene glycols such as tetraethylene glycol and triethylene glycol.

A synthetic polymer is preferred from the viewpoint of increasing the loading capacity of the inorganic ion adsorbent, while polyvinylpyrrolidone (PVP) or a polyethylene glycol is preferred from the viewpoint of increasing the porosity.

The weight-average molecular weight of the polyvinylpyrrolidone (PVP) or polyethylene glycol is preferably 400 to 35,000,000, more preferably 1,000 to 1,000,000 and even more preferably 2,000 to 100,000.

If the weight-average molecular weight is 400 or greater, a porous molded body with high surface openness will be obtained, and if it is 35,000,000 or lower, the viscosity of the slurry during molding will be low, tending to facilitate the molding.

The weight-average molecular weight of the water-soluble polymer can be measured by dissolving the water-soluble polymer in a predetermined solvent and analyzing it by gel permeation chromatography (GPC).

The amount of water-soluble polymer added may be such that the proportion of water-soluble polymer/(water-soluble polymer+porous molded body-forming polymer+good solvent for porous molded body-forming polymer) is preferably 0.1 mass % to 40 mass %, more preferably 0.1 mass % to 30 mass % and even more preferably 0.1 mass % to 10 mass %.

If the amount of water-soluble polymer added is 0.1 mass % or greater, it will be possible to uniformly obtain a porous molded body that includes a filamentous structure forming a network structure that is three-dimensionally connected on the outer surface and interior of the porous molded body. If the amount of water-soluble polymer added is 40 mass % or lower, the open area ratio on the outer surface will be satisfactory and the abundance of the inorganic ion adsorbent on the outer surface of the porous molded body will be high, to obtain a porous molded body that can reliably adsorb ions even with high-speed liquid flow treatment.

[Step (4): Molding Step]

In step (4), the slurry obtained in step (3) (molding slurry) is molded. The molding slurry is a mixed slurry comprising the porous molded body-forming polymer, the good solvent for the porous molded body-forming polymer, the inorganic ion adsorbent and if necessary a water-soluble polymer.

The form of the porous molded body of the embodiment may be any desired form such as particulate, filamentous, sheet-like, hollow fiber-like, cylindrical or hollow cylindrical, depending on the method of molding the molding slurry.

There are no particular restrictions on the method of molding a particulate form, such as spherical particles, and for example, it may be a rotation nozzle method in which the molding slurry housed in a vessel is ejected from nozzles provided on the side wall of the rotating vessel to form droplets. The rotating nozzle method allows molding into a particulate form with a uniform particle size distribution.

More specifically, the method may be atomization of the molding slurry from single-fluid or double-fluid nozzles for coagulation in a coagulating bath.

The nozzle diameters are preferably 0.1 mm to 10 mm and more preferably 0.1 mm to 5 mm. The droplets will be more easily ejected if the nozzle diameters are at least 0.1 mm, and the particle size distribution can be made uniform if it is 10 mm or smaller.

The centrifugal force is represented as the centrifugal acceleration, and it is preferably 5 G to 1500 G, more preferably 10 G to 1000 G and even more preferably 10 G to 800 G.

If the centrifugal acceleration is 5 G or greater the formation and ejection of the droplets will be facilitated, and if it is 1500 G or lower the molding slurry will be discharged without becoming filamentous, and widening of the particle size distribution can be inhibited. A narrow particle size distribution will result in uniform water flow channels when the porous molded body is packed into the column, providing an advantage whereby even when ultra high-speed water flow treatment is used there is no leakage of ions (the target of adsorption) from the start of water flow.

A method of molding into a filamentous or sheet form may be a method of extruding the molding slurry from a spinneret or die having that shape, and coagulating it in a poor solvent.

A method of molding into a hollow fiber porous molded body may be molding in the same manner as a method of molding the porous molded body into a filamentous or sheet form, but using a spinneret with an annular orifice.

A method of molding the porous molded body into a cylindrical or hollow cylindrical form, when extruding the molding slurry from a spinneret, may be cutting while coagulating in a poor solvent, or coagulating into a filamentous form followed by cutting.

[Step (5): Coagulation Step]

In step (5), the molded article with accelerated coagulation obtained in step (4) is further coagulated in a poor solvent to obtain a porous molded body.

<Poor Solvent>

The poor solvent for step (5) may be a solvent with a solubility of 1 mass % or lower for the porous molded body-forming polymer under the conditions in step (5), and examples include water, alcohols such as methanol and ethanol, ethers, and aliphatic hydrocarbons such as n-hexane and n-heptane. Water is most preferred as the poor solvent.

In step (5), the good solvent is carried over from the preceding steps, causing variation in the concentration of the good solvent at the start and end points of the coagulation step. The poor solvent may therefore have the good solvent added beforehand, and preferably the coagulation step is carried out while managing the concentration by separate addition of water or the like so as to maintain the initial concentration.

By adjusting the concentration of the good solvent it is possible to control the structure (the outer surface open area ratio and particle shapes) of the porous molded body.

When the poor solvent is water or a mixture of water with the good solvent for the porous molded body-forming polymer, the content of the good solvent for the porous molded body-forming polymer with respect to the water in the coagulation step is preferably 0 to 80 mass % and more preferably 0 to 60 mass %.

If the content of the good solvent for the porous molded body-forming polymer is 80 mass % or lower, a favorable effect for a satisfactory porous molded body shape will be obtained.

The temperature of the poor solvent is preferably 40 to 100° C., more preferably 50 to 100° C. and even more preferably 60 to 100° C., from the viewpoint of controlling the temperature and humidity of the spaces in the rotating vessel that causes ejection of the droplets by centrifugal force, as described below.

[Production Apparatus for Porous Molded Body]

When the porous molded body of the embodiment is in particulate form, the production apparatus comprises a rotating vessel that ejects droplets by centrifugal force and a coagulation tank that stores a coagulating solution, also optionally being provided with a cover that covers the space between the rotating vessel and the coagulation tank and comprising control means that controls the temperature and humidity in the space.

The rotating vessel that ejects droplets by centrifugal force is not restricted to one with a specific construction so long as it has the function of ejecting the molding slurry as spherical droplets by centrifugal force, and examples include known types of rotating discs or rotating nozzles.

With a rotating disc, the molding slurry is supplied to the center of the rotating disc and the molding slurry is developed into a film of uniform thickness along the surface of the rotating disc, and then divided into droplets by centrifugal force from the peripheral edges of the disc to eject the microdroplets.

A rotating nozzle either has a plurality of through-holes formed in the perimeter wall of a rotating vessel having a hollow disc shape, or it has nozzles attached through the perimeter wall, with the molding slurry being supplied into the rotating vessel while rotating the rotating vessel, and the molding slurry being discharged by centrifugal force from the through-holes or nozzles to form droplets.

The coagulation tank that stores the coagulating solution is not limited to any particular structure so long as it has a function allowing it to store the coagulating solution, and for example, it may be a coagulation tank with an open top side, as is commonly known, or a coagulation tank having a construction in which the coagulating solution is allowed to flow down naturally by gravity along the inner walls of the cylinder situated surrounding the rotating vessel.

A coagulation tank with an open top side is an apparatus that allows droplets ejected in the horizontal direction from the rotating vessel to fall down naturally, and traps droplets on the liquid surface of the coagulating solution stored in the open-top coagulation tank.

A coagulation tank with a construction in which the coagulating solution is allowed to flow down naturally by gravity along the inner walls of the cylinder surrounding the rotating vessel is an apparatus that discharges the coagulating solution at a roughly equivalent flow rate in the circumferential direction along the inner walls of the cylinder, and traps droplets in the coagulating solution flowing downward along the inner walls, causing them to coagulate.

The control means for the temperature and humidity in the space is provided with a cover that covers the space between the rotating vessel and coagulation tank, and it controls the temperature and humidity in the space.

The cover covering the space is not restricted to any particular construction so long as it has the function of isolating the space from the external environment and facilitating practical control of the temperature and humidity in the space, and it may be box-shaped, tubular or umbrella-shaped, for example.

The material of the cover may be stainless steel metal or plastic, for example. For isolation from the external environment, it may also be covered by a known type of insulation. The cover may also be partially provided with openings for temperature and humidity adjustment.

The means for controlling the temperature and humidity in the space is not limited to any particular means so long as it has the function of controlling the temperature and humidity in the space, and for example, it may be a heating machine such as an electric heater or steam heater, or a humidifier such as an ultrasonic humidifier or heating humidifier.

A preferred means in terms of construction is one that heats the coagulating solution stored in the coagulation tank and utilizes steam generated from the coagulating solution to control the temperature and humidity in the space.

A method of forming a coating layer of a biocompatible polymer on the surface of a porous molded body will now be described.

For this embodiment, a coating solution containing a PMEA- or a PVP-based polymer, for example, may be applied onto the surface of the porous molded body to form a coating film. For example, a PMEA coating solution can penetrate the pores formed in the porous molded body, allowing the PMEA to be added to the entire pore surface of the porous molded body without significantly altering the pore sizes on the surface of the porous molded article.

The solvent of the PMEA coating solution is not particularly restricted so long as it is a solvent that can dissolve or disperse the PMEA without dissolving the polymers such as the porous molded body-forming polymer of the porous molded body and the water-soluble polymer, but it is preferably water or an aqueous alcohol solution, for process safety and satisfactory handleability in the subsequent drying step. From the viewpoint of the boiling point and of toxicity, it is preferred to use water, an aqueous ethanol solution, an aqueous methanol solution or an aqueous isopropyl alcohol solution.

The solvent of the PVP coating solution is not particularly restricted so long as it is a solvent that can dissolve or disperse the PVP without dissolving the polymers such as the porous molded body-forming polymer of the porous molded body and the water-soluble polymer, but it is preferably water or an aqueous alcohol solution, for process safety and satisfactory handleability in the subsequent drying step. From the viewpoint of the boiling point and of toxicity, it is preferred to use water, an aqueous ethanol solution, an aqueous methanol solution or an aqueous isopropyl alcohol solution.

The type and composition of the solvent in the coating solution is selected as appropriate in relation to the polymer forming the porous molded body.

The PMEA concentration of the PMEA coating solution is not restricted, but as an example it may be 0.001 mass % to 1 mass %, and preferably 0.005 mass % to 0.2 mass %, of the coating solution.

The method of applying the coating solution is also not restricted, and an example is a method in which the porous molded body is packed into a suitable column (vessel) and flushed from the top with a coating solution containing PMEA, and compressed air is then used to remove the excess solution.

After subsequently washing with distilled water and substituting out the unnecessary solvent, it may be sterilized for use as a medical tool.

EXAMPLES

Examples and Comparative Examples will now be described, with the understanding that they are not limitative on the invention. The physical properties of the porous molded body and the performance of the blood purification device were measured as follows. The scope of the invention is not limited to the Examples described below, and various modifications may be implemented within the scope of the gist thereof.

[Metal Concentration Analysis]

The metal concentration in the physiological saline for injection was measured before encapsulation in the blood purification device and upon removal 3 months and 6 months after encapsulation, using an inductively coupled plasma mass spectrometer (iCAPQ by ThermoSCIENTIFIC). The amount of metal elution was the difference compared to the amount of metal in the physiological saline for injection before injection into the blood purification device.

[Mean Particle Size of Porous Molded Body and Mean Particle Size of Inorganic Ion Adsorbent]

The mean particle size of the porous molded body and the mean particle size of the inorganic ion adsorbent were measured using a laser diffraction/scattering particle size distribution analyzer (LA-950, trade name of Horiba Co.). The dispersing medium used was water. For measurement of samples using hydrated cerium oxide as the inorganic ion adsorbent, the refractive index used was the value for cerium oxide. Likewise, for measurement of samples using hydrated zirconium oxide as the inorganic ion adsorbent, the refractive index used was the value for zirconium oxide.

[Phosphorus Adsorption with Bovine Plasma]

The apparatus shown in FIG. 1 was used to measure the phosphorus adsorption by a column flow test with low-phosphorus serum using bovine plasma. Bovine plasma prepared to a low phosphorus level (0.7 mg/dL) was used for measurement of the amount of phosphorus adsorbed by the porous molded body (mg-P/mL-resin (porous molded body)) packed into a column (vessel) under conditions equivalent to common dialysis conditions (space velocity SV=120, 4 hours dialysis).

The phosphate ion concentration was measured by the molybdic acid direct method.

Phosphorus adsorption of 1.5 (mg-P/mL-resin) or greater with a flow speed of SV120 was judged to be high adsorption capacity and satisfactory as a phosphorus adsorbent.

[Amount of Microparticles]

A microparticle counter (KL-04 by Rion Co., Ltd.) was used for measurement of each evaluation sample. After discarding the first measured value, measurement was performed an additional 3 times and the average was recorded as the measured value.

Example 1

After loading 2000 g of cerium sulfate tetrahydrate (Wako Pure Chemical Industries, Ltd.) in 50 L of purified water, a stirring blade was used for dissolution, and then 3 L of 8 M caustic soda (Wako Pure Chemical Industries, Ltd.) was added dropwise at a rate of 20 ml/min to obtain a hydrated cerium oxide precipitate. The obtained precipitate was filtered with a filter press and then washed by flowing through 500 L of purified water, after which 80 L of ethanol (Wako Pure Chemical Industries, Ltd.) was additionally flowed through, replacing the water in the hydrated cerium oxide with ethanol. A 10 ml portion of the filtrate was sampled after filtration was complete, and the moisture content was measured with a Karl Fischer moisture content meter (CA-200, trade name of Mitsubishi Chemical Holdings Corp. Analytech Co., Ltd.), resulting in a moisture content of 5 mass % and an organic liquid replacement rate of 95 mass %. The hydrated cerium oxide containing the organic liquid was air dried to obtain dried hydrated cerium oxide.

The obtained dried hydrated cerium oxide was pulverized using a jet mill apparatus (SJ-100, trade name of Nisshin Engineering Inc.) under conditions with a pneumatic pressure of 0.8 MPa and a starting material feed rate of 100 g/hr, to obtain hydrated helium oxide powder having a mean particle size of 1.2 μm.

After adding 214.8 g of N-methyl-2-pyrrolidone (NMP, product of Mitsubishi Chemical Corp.), 146.4 g of pulverized hydrated cerium oxide powder (MOX) and 39.2 g of polyethersulfone (PES, product of Sumitomo Chemical Co., Ltd.), the mixture was heated to 60° C. in a dissolution tank and stirred to dissolution using a stirring blade, to obtain a homogeneous molding slurry solution.

The obtained molding slurry was supplied into a cylindrical rotating vessel with 4 mm-diameter nozzles opened in the side wall, and the vessel was rotated to form droplets from the nozzles by centrifugal force (15 G). The droplets were allowed to splash into a coagulation tank with an open top side storing a coagulating solution with an NMP content of 50 mass % with respect to water, that had been heated to 60° C., to coagulate the molding slurry.

Alkali cleaning and sorting were also carried out after ethanol replacement, to obtain a spherical porous molded body.

The particle size of the porous molded body was 537 μm, the bulk density was 0.45 g/ml-resin and the water content was 83.2%.

[Washing with Supercritical Fluid]

The obtained porous molded body was washed for 1 hour using a supercritical fluid comprising carbon dioxide (critical temperature: 304.1K, critical pressure: 7.38 MPa, device by ITEC Co., Ltd.).

[PMEA Coating]

A 1 mL portion of the obtained porous molded body was packed into a cylindrical vessel (having a glass filter set at the base, L (length)/D (cylinder diameter)=1.5). Next, 0.2 g of PMEA (Mn 20,000, Mw/Mn 2.4) was dissolved in an aqueous solution of 40 g ethanol/60 g water (100 g) to prepare a coating solution. The vessel packed with the porous molded body was held vertically and flushed from the top with the coating solution at a flow rate of 100 mL/min, contacting the coating solution with the porous molded body, after which it was washed with purified water.

After the purified water washing, the coating solution was sprayed into the vessel with air at 0.1 MPa, the module was placed in a vacuum dryer and vacuum dried for 15 hours at 35° C., and gamma sterilization was carried out at 25 kGy in an air atmosphere to fabricate a blood purification device.

[Column Flow Test with Low-Phosphorus Serum using Bovine Plasma]

Considering the intended use as a phosphorus adsorber after use of a dialyzer in dialysis treatment, it was decided to measure the phosphorus adsorption at a dialyzer outlet during dialysis treatment, with an inorganic phosphorus concentration of 0.2 to 1.0 mg/dl in blood. The phosphorus concentration in the test plasma solution was therefore adjusted.

Commercially available bovine serum was centrifuged (3500 rpm, 5 min) and 2000 mL of blood plasma supernatant was prepared. The phosphorus concentration in the blood plasma was 10.8 mg/dL.

The porous molded body obtained in Example 1 was added to half of the obtained blood plasma (1000 mL), and stirred for 2 hours at room temperature, after which it was centrifuged (3500 rpm, 5 min) to obtain approximately 950 mL of blood plasma with a phosphorus concentration of 0.

After mixing 35 mL of blood plasma with a phosphorus concentration of 10.8 mg/dL and 465 mL of blood plasma with a phosphorus concentration of 0, the mixture was centrifuged (3500 rpm, 5 min) to obtain 495 mL of blood plasma with a phosphorus concentration of 0.8 mg/dL, as supernatant.

The blood purification device obtained in Example 1 was incorporated as shown in FIG. 1, and 450 mL of the obtained blood plasma was flowed through at a flow rate of 2 mL/min, sampling 10 mL as the first fraction and 20 mL for each sample thereafter. Based on usual average dialysis conditions of 4 hours of dialysis at a flow rate Qb=200 mL/min, the total blood flow was 200 mL×4 hours=48,000 mL, and assuming the blood cell component to be Ht=30%, the blood plasma flow was 33,600 mL. The amount of liquid flow was 340 mL in this case, since the experiment was at a 1/100 scale.

The phosphorus adsorption of the porous molded body at a blood plasma flow volume of 350 mL was 2.91 mg-P/mL-resin.

[Evaluation Results]

The performance of the obtained blood purification device is shown in Table 1. The blood purification device had high phosphorus adsorption capacity, was safely usable, and its number of microparticles and metal elution conformed to the approval standards for artificial kidney devices.

Example 2

After adding 217.6 g of NMP and 31.6 g of PES to 31.6 g of polyvinylpyrrolidone (PVP, K90 by BASF Corp.) as the hydrophilic polymer (water-soluble polymer) and 119.2 g of MOX, the same procedure was carried out as in Example 1 to obtain a spherical porous molded body.

The performance of the obtained blood purification device is shown in Table 1. The blood purification device had high phosphorus adsorption capacity, was safely usable, and its number of microparticles and metal elution conformed to the approval standards for artificial kidney devices.

Example 3

A blood purification device was fabricated in the same manner as Example 1, except that PMEA was not coated. The performance of the obtained blood purification device is shown in Table 1.

Comparative Example 1

A blood purification device was fabricated in the same manner as Example 1, except that washing with a supercritical fluid was not carried out. The properties of the obtained blood purification device are shown in Table 1.

Comparative Example 2

A blood purification device was fabricated in the same manner as Example 1, except that alkali cleaning was not carried out after coagulation of the molding slurry. The properties of the obtained blood purification device are shown in Table 1.

TABLE 1

| Construction | Example 1 | Example 2 | Example 3 | Comparative Example 1 | Comparative Example 2 |
|---|---|---|---|---|---|
| Porous molded body-forming polymer/weight (wt %) | PES/9.8 | PES/7.9 | PES/9.8 | PES/9.8 | PES/9.8 |
| Water-soluble polymer/weight (wt %) | — | PVP/7.9 | — | — | — |
| Inorganic ion adsorbent/weight (wt %) | Ce/36.6 | Ce/29.8 | Ce/36.6 | Ce/36.6 | Ce/36.6 |
| Solvent/weight (wt %) | NMP/53.7 | NMP/54.4 | NMP/53.7 | NMP/53.7 | NMP/53.7 |
| Particle size of inorganic ion adsorbent (μm) | 1.2 | 1.2 | 1.2 | 1.2 | 1.2 |
| Concentration of Mg, Al, Ti, V, Cr, Mn, Ni, Cu, Zn, Ga, Rb, Sr, Y, Zr, Mo, Ru, Ag, Cd, Sn, Cs, La, Pr, Sm, Gd, Tb, Ta, Au, Tl, Co, In, Bi (ppb) | <0.1 | <0.1 | <0.1 | <0.1 | 0.2 |

TABLE 1-continued

| Construction | | Example 1 | Example 2 | Example 3 | Comparative Example 1 | Comparative Example 2 |
|---|---|---|---|---|---|---|
| Fe concentration (ppb) | | <0.1 | <0.1 | <0.1 | <0.1 | 20 |
| Ba, Nd, Pb concentration (ppb) | | <1 | <1 | <1 | <1 | 3 |
| Ce concentration (ppb) | | <1 | <1 | <1 | <1 | 9 |
| Particle size (μm) | | 537 | 543 | 537 | 538 | 537 |
| Blood phosphorus adsorption (mg/ml-resin) | | 2.91 | 3.94 | 2.91 | 2.88 | 2.95 |
| *Granulatable | | Yes | Yes | Yes | Yes | Yes |
| Number of microparticles after elapse of 1 week | ≥10 μm [number] | 5 | 2 | 5 | 20 | 5 |
| | ≥25 μm [number] | 0 | 0 | 1 | 3 | 0 |
| Number of microparticles after elapse of 3 months | ≥10 μm [number] | 8 | 4 | 10 | 30 | 9 |
| | ≥25 μm [number] | 1 | 1 | 2 | 8 | 1 |
| Number of microparticles after elapse of 6 months | ≥10 μm [number] | 9 | 6 | 16 | 66 | 12 |
| | ≥25 μm [number] | 2 | 1 | 3 | 10 | 2 |

*Granulatable: Judged whether spherical shapes can be obtained during granulation.

Example 4

A blood purification device was fabricated in the same manner as Example 2, except that for PMEA coating, 1.0 g of PMEA was dissolved in an aqueous solution of 40 g methanol/60 g water (100 g) to prepare a coating solution, and washing with a supercritical fluid was not carried out. The performance of the obtained blood purification device is shown in Table 2. The blood purification device had high phosphorus adsorption capacity, was safely usable, and its number of microparticles and metal elution conformed to the approval standards for artificial kidney devices.

Example 5

A blood purification device was fabricated in the same manner as Example 2, except that hydrated zirconium oxide (R Zirconium Hydroxide, trade name of Daiichi Kigenso Kagaku Kogyo Co., Ltd.) was used instead of MOX. The performance of the obtained blood purification device is shown in Table 2. The blood purification device had high phosphorus adsorption capacity, was safely usable, and its number of microparticles and metal elution conformed to the approval standards for artificial kidney devices.

Example 6

A blood purification device was fabricated in the same manner as Example 2, except that lanthanum oxide (product of Nacalai Tesque, Inc.) was used instead of MOX. The performance of the obtained blood purification device is shown in Table 2. The blood purification device had high phosphorus adsorption capacity, was safely usable, and its number of microparticles and metal elution conformed to the approval standards for artificial kidney devices.

Example 7

A blood purification device was fabricated in the same manner as Example 2, except that neodymium carbonate (Neodymium Carbonate Octahydrate, trade name of Fujifilm Wako Chemical Corp.) was used instead of MOX. The performance of the obtained blood purification device is shown in Table 2. The blood purification device had high phosphorus adsorption capacity, was safely usable, and its number of microparticles and metal elution conformed to the approval standards for artificial kidney devices.

Example 8

A blood purification device was fabricated in the same manner as Example 1, except that the molding slurry solution used was a mixed solution comprising 220 g of NMP, 200 g of MOX, 4 g of PVP, and 10 g of a copolymer with limiting viscosity [η]=1.2 (organic polymer resin, PAN), comprising 91.5 wt % acrylonitrile, 8.0 wt % methyl acrylate and 0.5 wt % sodium methacrylsulfonate. The performance of the obtained blood purification device is shown in Table 2. The blood purification device had high phosphorus adsorption capacity, was safely usable, and its number of microparticles and metal elution conformed to the approval standards for artificial kidney devices.

Example 9

A blood purification device was fabricated in the same manner as Example 1, except that the molding slurry solution used was a mixed solution comprising 160 g of dimethyl sulfoxide (DMSO, product of Kanto Kagaku Co., Ltd.) as the good solvent for the organic polymer resin, 20 g of ethylene-vinyl alcohol copolymer (EVOH, SOARNOL E3803, trade name of Nippon Synthetic Chemical Industry Co., Ltd.) as the organic polymer resin, 4 g of PVP and 200 g of MOX. The performance of the obtained blood purification device is shown in Table 2. The blood purification device had high phosphorus adsorption capacity, was safely usable, and its number of microparticles and metal elution conformed to the approval standards for artificial kidney devices.

Example 10

A blood purification device was fabricated in the same manner as Example 1, except that the molding slurry solution used was a mixed solution comprising 220 g of DMSO, 28 g of poly(methyl methacrylate) (PMMA, DIANAL BR-77, trade name of Mitsubishi Chemical Corp.) as the organic polymer resin, 32 g of PVP and 120 g of MOX. The performance of the obtained blood purification device is shown in Table 2. The blood purification device had high phosphorus adsorption capacity, was safely usable, and its number of microparticles and metal elution conformed to the approval standards for artificial kidney devices.

TABLE 2

| Construction | | Example 4 | Example 5 | Example 6 | Example 7 | Example 8 | Example 9 | Example 10 |
|---|---|---|---|---|---|---|---|---|
| Porous molded body-forming polymer/weight (wt %) | | PES/7.9 | PES/7.9 | PES/7.9 | PES/7.9 | PAN/2.3 | EVOH/5.2 | PMMA/7.0 |
| Water-soluble polymer/weight (wt %) | | PVP/7.9 | PVP/7.9 | PVP/7.9 | PVP/7.9 | PVP/0.9 | PVP/1.0 | PVP/8.0 |
| Inorganic ion adsorbent/weight (wt %) | | Ce/29.8 | Zr/29.8 | La/29.8 | Nd/29.8 | Ce/46.1 | Ce/52.1 | Ce/30.0 |
| Solvent/weight (wt %) | | NMP/54.4 | NMP/54.4 | NMP/54.4 | NMP/54.4 | NMP/50.7 | DMSO/41.7 | DMSO/55.0 |
| Particle size of inorganic ion adsorbent (μm) | | 1.2 | 1.2 | 1.2 | 1.2 | 1.2 | 1.2 | 1.2 |
| Concentration of Mg, Al, Ti, V, Cr, Mn, Ni, Cu, Zn, Ga, Rb, Sr, Y, Zr, Mo, Ru, Ag, Cd, Sn, Cs, La, Pr, Sm, Gd, Tb, Ta, Au, Tl, Co, In, Bi (ppb) | | <0.1 | <0.1 | <0.1 | <0.1 | <0.1 | <0.1 | <0.1 |
| Fe concentration (ppb) | | <0.1 | <0.1 | <0.1 | <0.1 | <0.1 | <0.1 | <0.1 |
| Ba, Nd, Pb concentration (ppb) | | <1 | <1 | <1 | <1 | <1 | <1 | <1 |
| Ce concentration (ppb) | | <1 | <1 | <1 | <1 | <1 | <1 | <1 |
| Particle size (μm) | | 539 | 536 | 533 | 535 | 371 | 533 | 537 |
| Blood phosphorus adsorption (mg/ml-resin) | | 1.80 | 1.92 | 9.88 | 9.17 | 2.30 | 1.64 | 1.54 |
| *Granulatable | | Yes | Yes | Yes | Yes | Yes | Yes | Yes |
| Number of microparticles after elapse of 1 week | ≥10 μm [number] | 22 | 2 | 8 | 13 | 2 | 4 | 6 |
| | ≤25 μm [number] | 2 | 0 | 2 | 3 | 0 | 0 | 1 |
| Number of microparticles after elapse of 3 months | ≥10 μm [number] | 23 | 3 | 9 | 16 | 2 | 4 | 8 |
| | ≤25 μm [number] | 2 | 0 | 3 | 3 | 0 | 0 | 1 |
| Number of microparticles after elapse of 6 months | ≥10 μm [number] | 24 | 3 | 10 | 19 | 2 | 4 | 8 |
| | ≤25 μm [number] | 3 | 1 | 3 | 3 | 0 | 0 | 1 |

*Granulatable: Judged whether spherical shapes can be obtained during granulation.

INDUSTRIAL APPLICABILITY

Since the blood purification device of the invention has high phosphorus adsorption capacity and safe usability, it can be suitably used in therapy for periodic removal of phosphorus that has accumulated in the body.

REFERENCE SIGNS LIST

1 Thermostatic bath
2 Laboratory bench
3 Pump
4 Column containing porous absorber (phosphorus absorbent)
5 Pressure gauge
6 Sampling

The invention claimed is:

1. A blood purification device comprising a porous molded body that includes an inorganic ion adsorbent, wherein the concentrations of Mg, Al, Ti, V, Cr, Mn, Fe, Ni, Cu, Zn, Ga, Rb, Sr, Y, Zr, Mo, Ru, Ag, Cd, Sn, Cs, La, Pr, Sm, Gd, Tb, Ta, Au, Tl, Co, In and Bi are all 0.1 ppb or lower and the concentrations of Ba, Nd, Pb and Ce are all 1 ppb or lower, in physiological saline for injection in the blood purification device at 3 months and 6 months after opening the physiological saline for injection, while the number of microparticles with sizes of 10 μm or greater is no more than 25 and the number of microparticles with sizes of 25 μm or greater is no more than 3, in 1 mL of the physiological saline for injection at 3 months and 6 months after the same physiological saline for injection has been encapsulated in the blood purification device,
wherein the porous molded body is coated with a first biocompatible polymer of polymethoxyethyl acrylate (PMEA), and
wherein the blood purification device is prepared by washing the porous molded body with a supercritical fluid or subcritical fluid to remove microparticles and trace metals.

2. The blood purification device according to claim 1, wherein the porous molded body is composed of a porous molded body-forming polymer, a hydrophilic polymer and an inorganic ion adsorbent.

3. The blood purification device according to claim 2, wherein the porous molded body-forming polymer is an aromatic polysulfone.

4. The blood purification device according to claim 2 or 3, wherein the hydrophilic polymer is a second biocompatible polymer.

5. The blood purification device according to claim 4, wherein the second biocompatible polymer is a polyvinylpyrrolidone (PVP)-based polymer.

6. The blood purification device according to claim 1 or 2, wherein the inorganic ion adsorbent contains at least one metal oxide represented by the following formula (1):

$$MN_xO_n \cdot mH_2O \qquad (1)$$

wherein x is 0 to 3, n is 1 to 4, m is 0 to 6, and M and N are metal elements selected from the group consisting of Ti, Zr, Sn, Sc, Y, La, Ce, Pr, Nd, Sm, Eu, Gd, Tb, Dy, Ho, Er, Tm, Yb, Lu, Al, Si, Cr, Co, Ga, Fe, Mn, Ni, V, Ge, Nb and Ta, and are different from each other.

7. The blood purification device according to claim 6, wherein the metal oxide is selected from among the following groups (a) to (c):
(a) hydrated titanium oxide, hydrated zirconium oxide, hydrated tin oxide, hydrated cerium oxide, hydrated lanthanum oxide and hydrated yttrium oxide;
(b) complex metal oxides comprising at least one metal element selected from the group consisting of titanium, zirconium, tin, cerium, lanthanum, neodymium and yttrium and at least one metal element selected from the group consisting of aluminum, silicon and iron; and
(c) activated alumina.

8. A method for producing the blood purification device according to claim 1, comprising a step of washing the porous molded body containing the inorganic ion adsorbent with a supercritical fluid or subcritical fluid, and then coating the surface with PMEA.

* * * * *